US012597153B2

(12) United States Patent
　　Merritt et al.

(10) Patent No.: US 12,597,153 B2
(45) Date of Patent: Apr. 7, 2026

(54) METHOD FOR OPTICALLY CALIBRATING AN INSTRUMENT DRILL TIP

(71) Applicant: X-Nav Technologies, LLC, Lansdale, PA (US)

(72) Inventors: Scott A. Merritt, Green Lane, PA (US); Justin Blaber, Lowell, MA (US); Sarah O'Brien, Pottstown, PA (US)

(73) Assignee: X-Nav Technologies, LLC, Lansdale, PA (US)

( * ) Notice: Subject to any disclaimer, the term of this patent is extended or adjusted under 35 U.S.C. 154(b) by 196 days.

(21) Appl. No.: 18/659,793

(22) Filed: May 9, 2024

(65) Prior Publication Data

US 2025/0349021 A1　　Nov. 13, 2025

(51) Int. Cl.
　　*A61B 17/16* 　　(2006.01)
　　*A61B 34/10* 　　(2016.01)
　　*G06T 7/13* 　　(2017.01)
　　*G06T 7/593* 　　(2017.01)
　　*G16H 40/40* 　　(2018.01)
　　*A61B 17/00* 　　(2006.01)

(52) U.S. Cl.
　　CPC .......... *G06T 7/596* (2017.01); *A61B 17/1615* (2013.01); *A61B 34/10* (2016.02); *G06T 7/13* (2017.01); *G16H 40/40* (2018.01); *A61B 2017/00057* (2013.01); *A61B 2017/00725* (2013.01); *A61B 2034/102* (2016.02); *G06T 2207/10012* (2013.01)

(58) Field of Classification Search
CPC .... A61B 2017/00725; A61B 2034/102; A61B 34/10
See application file for complete search history.

(56) References Cited

U.S. PATENT DOCUMENTS

| | | | |
|---|---|---|---|
| 9,402,691 B2 | 8/2016 | Merritt et al. | |
| 9,943,374 B2 | 4/2018 | Merritt et al. | |
| 10,350,008 B2 | 7/2019 | Gibbs et al. | |
| 11,510,638 B2 | 11/2022 | Merritt | |
| 2020/0051280 A1* | 2/2020 | Urban | G06T 7/50 |

* cited by examiner

*Primary Examiner* — Samuel S Hanna
(74) *Attorney, Agent, or Firm* — Faegre Drinker Biddle & Reath LLP

(57) ABSTRACT

A visual guidance system for use in a surgical procedure include a calibration operation of a tip of a surgical drill. In particular, the system includes capturing images of a drill tip and generating a reconstruction volume shape of the drill tip to enable tracking of the drill tip. The system captures images of the drill tip in tilting motion to determine cutting edge contour data of the drill tip. The system further captures images of the drill tip in rotation and identifies point cloud data of the drill tip. The system further includes generating a three-dimensional surface data of the drill tip, a cutting plane, and a cutting edge contour of the drill tip. Given the three dimensional surface data and plane data, the system further generates guidance data for providing a navigation on surgical procedure using three-dimensional graphical representation of the surgical drill.

20 Claims, 11 Drawing Sheets

METHOD FOR OPTICALLY CALIBRATING AN INSTRUMENT DRILL TIP

FIELD OF THE INVENTION

The present invention is directed to calibrating instruments, such as surgical tools, and, more specifically, to a method for determining information about an instrument drill tip using an optical system.

BACKGROUND

During a surgical procedure, the tip of a surgical instrument, such as a drill tip and a cutter tip with a specific shape, serves a specific function. In an image-guided surgical procedure, accuracy of operating the surgical instrument impacts outcome of operations. A system for navigating the surgical procedure by providing images needs to accurately track position of a surgical tip being used. The system needs to track a location of the tip with accuracy and notify in any visual displays that are configured to show in real-time a representation of the surgical procedure.

Calibrating the tip (e.g., a drill tip) of a surgical instrument enables navigation of placing and moving the tip of a surgical instrument with accuracy. The calibration of a drill tip takes place prior to or during a surgical procedure, as necessary. During the calibration, the system determines a shape, a position, and other features of the drill tip.

Traditional systems measure drill lengths for providing a guidance during a surgical procedure. Because of a limitation information available for calibration, the tradition systems suffered an issue of navigating use of the drill with accuracy in a three-dimensional space. There have been needs to enhance the guidance based on additional data of the drill tip.

It is with respect to these and other general considerations that the aspects disclosed herein have been made. Although relatively specific problems may be discussed, it should be understood that the examples should not be limited to solving the specific problems identified in the background or elsewhere in this disclosure.

SUMMARY

Aspects of the present disclosure relate to a system and a method for calibrating a drill tip. For example, the disclosed aspects improve accuracy of calibrating the drill tip by automatically measuring the drill tip, such as with a stereographic imaging system, and constructing a three-dimensional shape of the drill tip. The disclosed aspects enable a surgical procedure navigation system to perform calibration tasks interactively, enabling tracking of positions and movements of the drill tip with accuracy and to navigate use of the drill tip with accuracy during a surgical procedure.

This Summary introduces a selection of concepts in a simplified form, which is further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the following description and, in part, will be apparent from the description, or may be learned by practice of the disclosure.

BRIEF DESCRIPTION OF THE DRAWINGS

For the purpose of illustrating the invention, the drawings show a form of the invention that is presently preferred.

However, it should be understood that the invention is not limited to the precise arrangement and instrumentalities show in the drawings.

FIGS. 5A-B illustrate example of the reconstructed main cutting plane and cutting surface of the tip of the according to the present invention.

DETAILED DESCRIPTION

Figure 1:
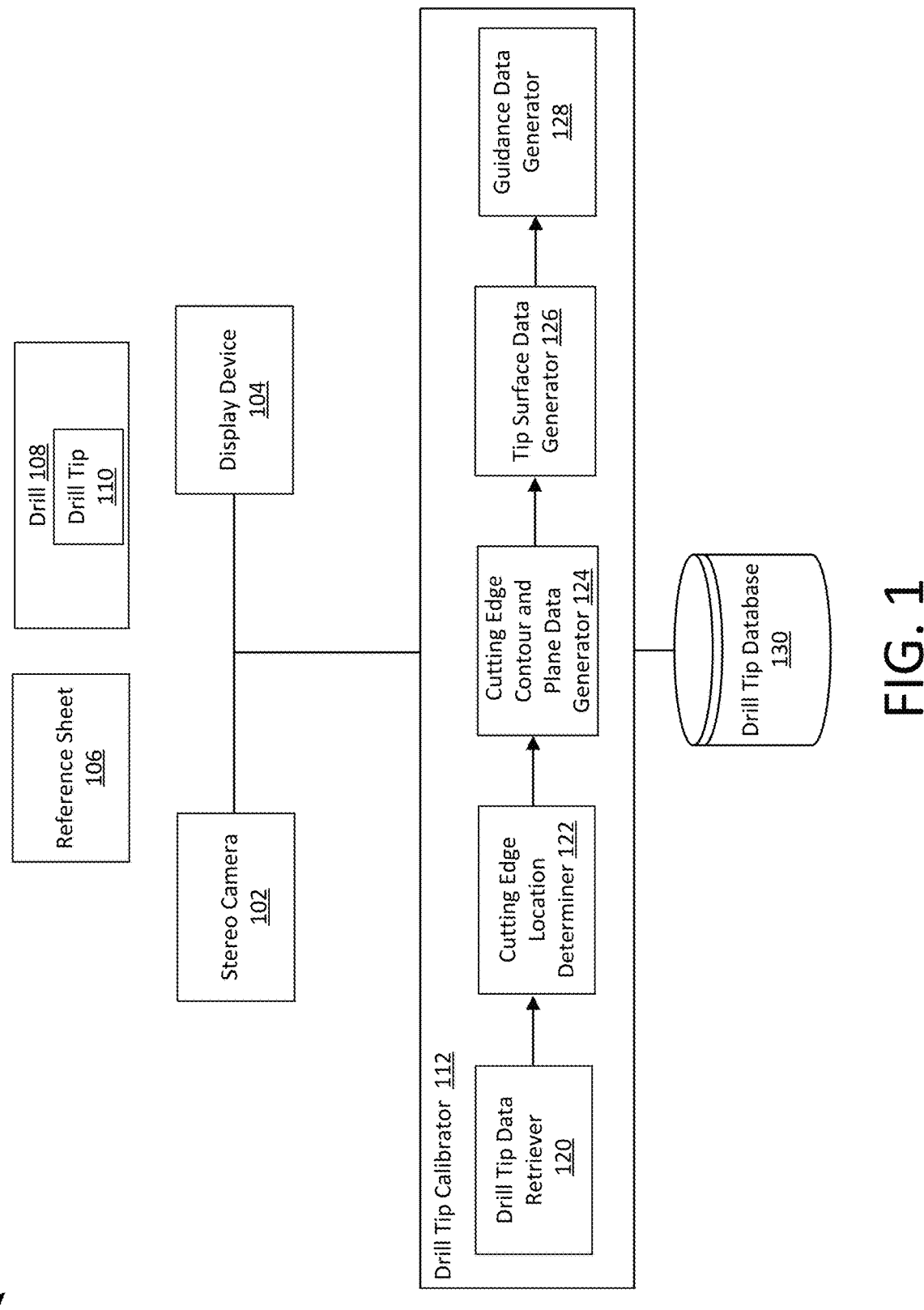
FIG. 1 illustrates an overview of an embodiment for detecting and analyzing features of a drill tip according to the present invention.

U.S. Pat. Nos. 9,402,691 and 9,943,374, which are incorporated herein by reference in their entireties, describe an optical tracking system configured to detect and track patterns.

In the following detailed description, references are made to the accompanying drawings that form a part hereof, and in which are shown by way of illustrations specific embodiments or examples. These aspects may be combined, other aspects may be utilized, and structural changes may be made without departing from the present disclosure. Embodiments may be practiced as methods, systems or devices. Accordingly, embodiments may take the form of a hardware implementation, an entirely software implementation, or an implementation combining software and hardware aspects. The following detailed description is therefore not to be taken in a limiting sense, and the scope of the present disclosure is defined by the appended claims and their equivalents.

Recent advances made in technologies of image recognition and graphical data rendition have enabled introducing systems and tools to navigate operations of a surgical procedure in medical and other areas of practices. For examples, some systems and tools capture a video of the operations using one or more monaural or stereo video cameras and displays magnified areas of the operations. Some other systems and tools provide a real-time guidance on operating a tool with precision during the operation. In aspects, the guidance includes a position and an angle of placing the tool at a specific area of the operation. The guidance may further include a direction, speed, and a distance of moving the tool during the operation.

Examples of the surgical tools include, but not limited to, a piezoelectric drill, a positional detection probe, etc. The piezoelectric drill includes a drill tip, a stem, and a handle. The drill tip and stem are typically integral with one another and removable from the handle. In aspects, the piezoelectric drill operates by rapidly moving the drill tip at a piezoelectric ultrasonic frequency and cuts a target affected area. In some aspects, the surgical navigation system navigates a user undertaking a surgical procedure by displaying a current position and angle, and a target position and angle, in three-dimensional graphics rendering form to selectively cut materials in target areas. Accordingly, a result of calibration of the drill tip affects an accuracy of the navigation.

Embodiments relate to calibrating a drill tip. In particular, the present technology is directed to determining a cutting edge contour and a cutting plane of a selected drill tip and reconstructing a three-dimensional surface data of the drill tip based on interactive calibration operations with the user. In aspects, the reconstruction of the three-dimensional surface data is based on reconstructing a volume shape of the drill tip and dynamically determining orthogonal and horizontal planes of symmetry of the drill tip.

Steps of reconstructing the three-dimensional surface data may include capturing feature points of the drill tip from frames of image data in a video as the user moves the drill tip specifically as instructed. Examples of the instructed movement may include rocking motion and rotation of the drill tip. Given the captured feature points of the drill tip, the steps may further include performing statistical analysis of the captured feature points to reconstruct the three-dimensional shape data. The calibration operations according to the present technology enables generating the three-dimensional shape data of the drill tip with accuracy and with case of operations by the user.

Types of surgical procedure may include, but not limited to a dental procedure, a medical procedure that involves cutting a bone, and other general procedures including placement and removal of a cast that hold a part of a body.

FIG. 1 illustrates an overview of an embodiment for detecting and analyzing features of a drill tip according to the present invention. In aspects, an example system includes stereo camera 102, display device 104, reference sheet 106, drill 108 with drill tip 110, and drill tip calibrator 112. Stereo cameras are well known and, as used herein, can be a single camera with two separate lenses or could be two separate camera units, each with its own lens. The stereo camera 102 captures frames of image data (e.g., as video data) of the drill 108 and the reference sheet 106 during calibration of the drill 108 and may further capture video data during a surgical procedure. In aspects, the stereo camera 102 captures the video data of the operational scenes in stereo (i.e., stereographic images) to enable generating three-dimensional images of the drill 108 with accuracy based on a differential in stereo viewing angles used by the stereo camera 102. The display device 104 displays a graphical user interface to interactively calibrate the drill 108. The drill tip calibrator 112 performs an interactive task of calibrating the drill 108. The drill 108 includes a drill tip 110 that is removable from the drill 108.

In aspects, the drill tip calibrator 112 interactively performs calibration of the drill tip 110 of the drill 108. The calibration includes interactive user operations of placing and moving the drill 108 and drill tip. At least a part of the operations includes use of the reference sheet 106 for determining a position and an angle of the drill tip. The drill tip calibrator 112 includes drill tip data retriever 120, cutting edge location determiner 122, cutting edge contour and plane data generator 124, tip surface data generator 126, and guidance data generator 128. The drill tip calibrator 112 accesses a drill tip database 130.

In aspects, the reference sheet 106 indicates a grid pattern of contrasting shapes (i.e., a checkerboard pattern). The pattern may be a pattern as described in U.S. Pat. No. 9,943,374. Although a reference "sheet" is referred to herein, the component is preferably a surface that includes a pattern containing optically detectable features. The grid pattern may be used as reference for determining a position and an angle of the drill tip 110 when the user places the drill tip 110 of the drill 108 on the reference sheet 106. The drill tip calibrator 112 analyzes captured frames of images including the drill tip 110 and the grid pattern to determine edges between a contrasting shape of the drill tip 110. The drill tip calibrator 112 further overlays, draws and/or places lines extending along a series of adjacent edges. The drill tip calibrator 112 is also programmed to determine breaks in lines/edges, as well as features of a component captured in the images (such as contour). Given the determined features, the processor may calculate or determine characteristics (e.g., diameter, shape, etc.) of the drill tip 110.

The drill tip data retriever 120 retrieves information of the drill tip 110 of the drill 108 from the drill tip database 130. In aspects, the present technology includes interactively receiving a selection of the drill 108 and/or the drill tip 110 from a set of drills and/or drill tips for calibration using a graphical user interface. The drill tip 110 as selected is subject to calibration as detailed in the embodiments.

The cutting edge location determiner 122 interactively determines a location of a cutting edge of the drill tip 110 from one or more frames of image data captured by the stereo camera 102 as video data. In aspects, the image data depicts the drill tip 110 that is placed on or pointing to a pattern object on the reference sheet 106. The cutting edge represents an edge along which the drill tip 110 cuts a material (e.g., a tooth, a tissue, a material) in a target area during a procedure. In aspects, the cutting edge location determiner 122 interactively instructs a user to place the tip of the drill tip 110 of the drill 108 on the reference sheet 106 as the stereo camera 102 captures the drill tip 110.

Figures 3A, 3B:
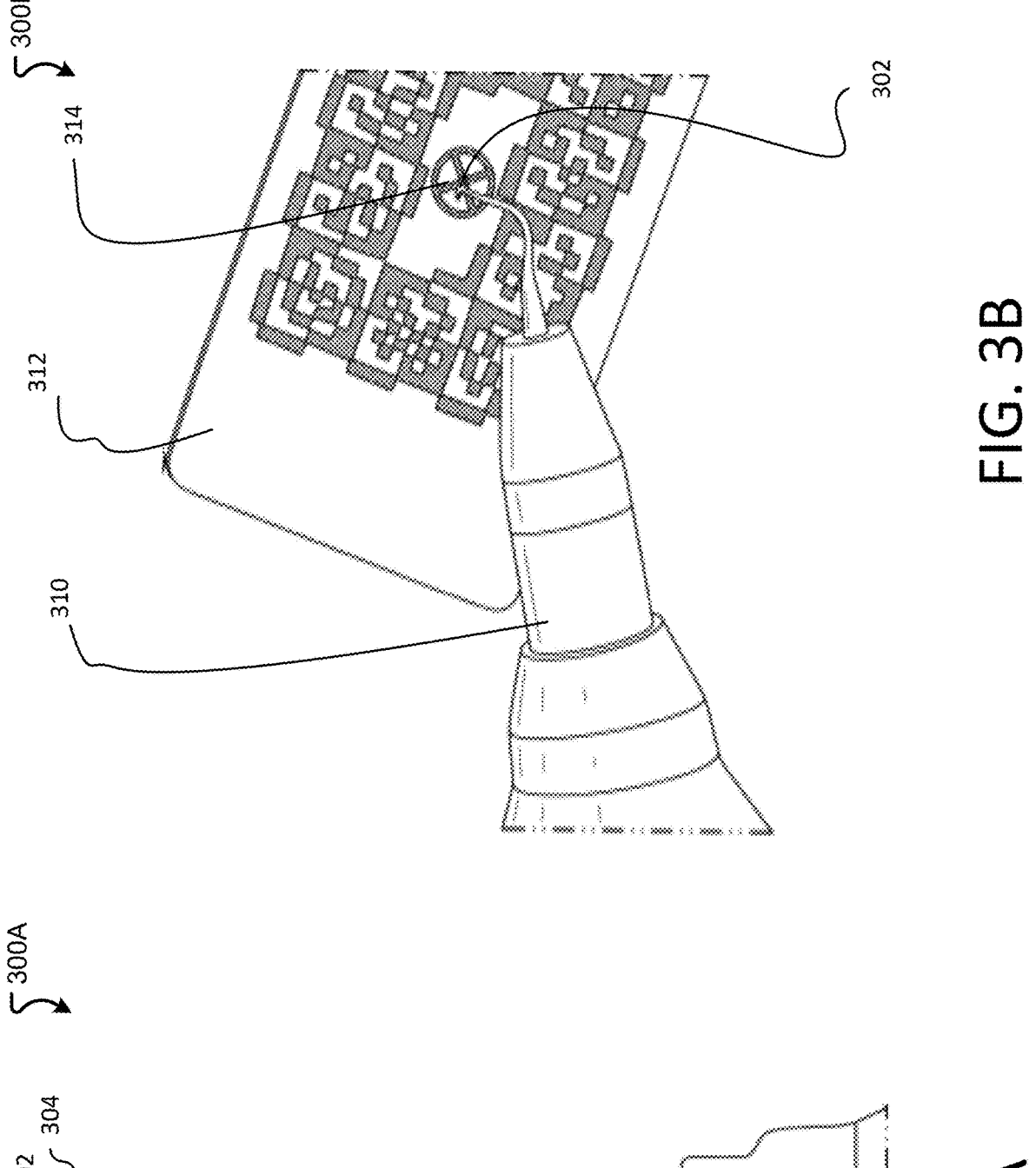
FIG. 3A illustrates an example graphical image of a selected drill according to an embodiment of the invention.
FIG. 3B illustrates an example graphical image depicting a drill and a reference sheet used to detect a location of a drill tip and rocking the drill at the tip according to an embodiment of the invention.
Figures 4A, 4B, 4C, 4D:
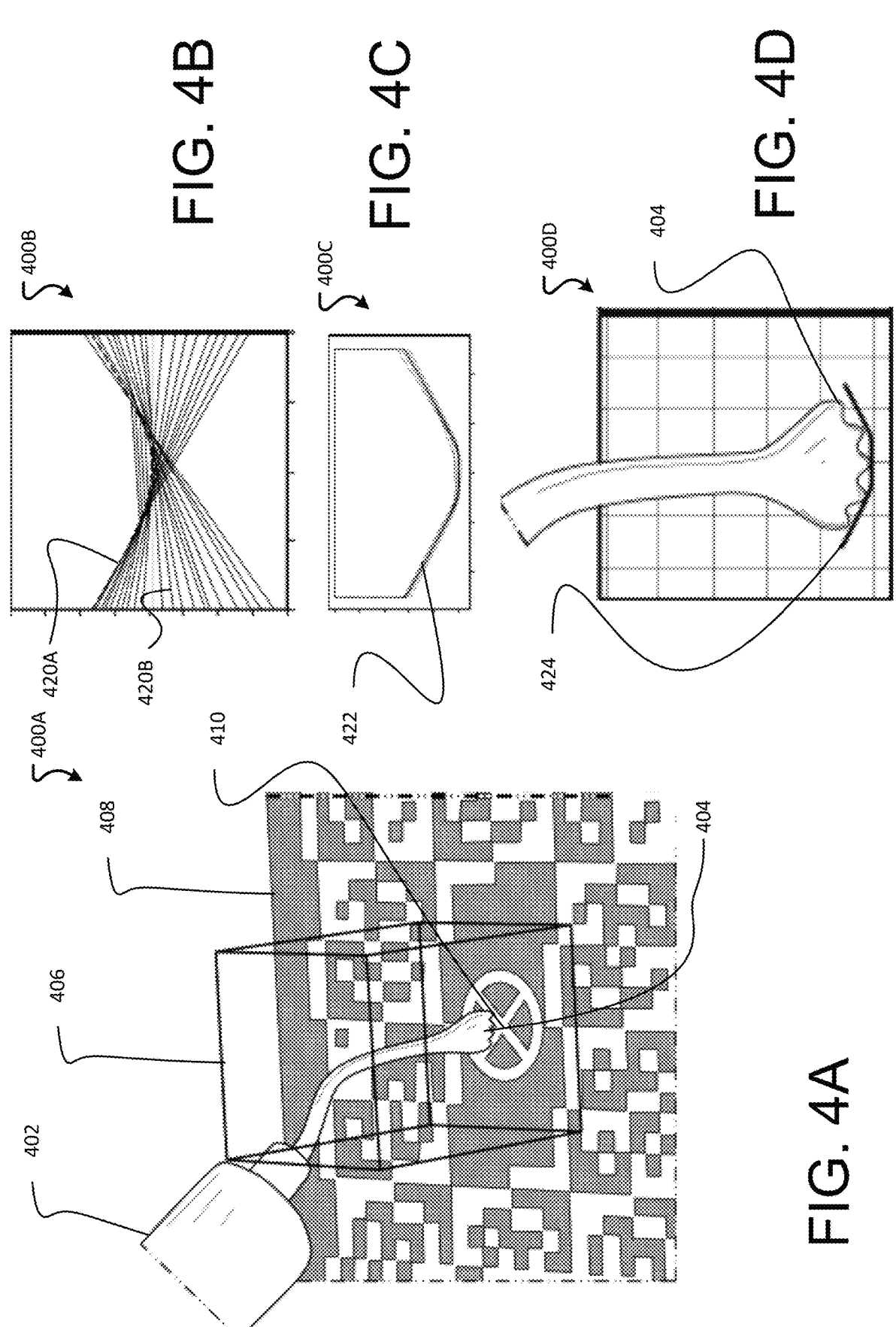
FIG. 4A illustrates an example reconstruction volume shape generated about a drill tip of a drill according to the present invention.
FIG. 4B illustrates example data points of planes tangent to the cutting edge of the drill tip of the drill according to the present invention.
FIG. 4C illustrates combined example data points to determine edge contour data of the drill tip of the drill according to the present invention.
FIG. 4D illustrates an example drill tip with edge contour data according to the present invention.

In aspects, the cutting edge location determiner 122 provides an instruction to a user to hold the drill 108 in a way that the drill tip 110 points at a predetermined place (e.g., a center mark 314 as shown in FIG. 3B) on the reference sheet 106 for a predetermined period of time causing the cutting edge location determiner 122 to compute a transform between a reconstruction volume shape and the drill tracker 208. In examples, the reconstruction volume shape represents a rectangular wireframe in a three-dimensional space. The reconstruction volume shape is sized to include the drill tip 110 and a stem portion of the drill 108. In examples, the cutting edge location determiner 122 analyzes the image data and determines a location and an angle of the drill tip 110 in the image data. Given the identified location and angle of the drill tip 110, the cutting edge location determiner 122 generates a three-dimensional rectangular shape (i.e., a reconstruction volume shape 406 fixed to the center mark 410 of the reference sheet 408 as shown in FIG. 4A) in the image data. The three dimensional rectangular shape includes the stem and the drill tip 110. The drill tip 110 is located on the inner bottom surface of the reconstruction volume shape.

The cutting edge contour and plane data generator 124 generates a cutting edge contour data of the drill tip 110 and a plane data of the drill tip 110. In aspects, the cutting edge contour and plane data generator 124 interactively receives frames of image data of the drill tip 110 as the user interactively tilts the drill tip of the drill, thereby changing the angle of the camera relative to the drill tip for use in 3D reconstruction of the drill tip. In examples, the cutting edge contour and plane data generator 124 instructs the user to pivot the drill at the drill tip in a back and forth, rocking motion. Given the frames of image data with the tip tilting in varying angles in the rocking motion, the cutting edge contour and plane data generator 124 determines an edge of the drill tip 110 in varying angles. In aspects, the rocking motion of the drill tip 110 along the cutting edge of the drill tip 110 on the reference sheet 106 enables computing a plane that is tangent to the cutting edge of the drill tip 110.

The tip surface data generator 126 generates a three-dimensional surface data of the drill tip 110. In aspects, the tip surface data generator 126 uses the horizontal and vertical planes of symmetry of the drill tip 110 to compute the overall cutting edge contour of the drill tip 110. The tip surface data generator 126 superimposes the cutting edge contour data obtained from one or more tilting motions of the rocking motion in a three-dimensional space. In aspects, the tip surface data generator 126 interactively instructs the user to rotate the drill tip 110 of the drill 108. Accordingly, the user rotates the drill tip 110 in front of a known type of background. In aspects, the known type includes a plain white background. Another type of background may be fiducial marker grid background or a backlight. In aspects, the tip surface data generator 126 computes a reconstruction volume shape (i.e., the rectangular wireframe) and obtains a sub image containing the drill tip 110 in the known background.

In aspects, the tip surface data generator 126 obtains a segmentation of the drill tip 110 from the known background and connects data points of the drill tip 110 from distinct view angles as the user rotates the drill tip 110. In aspects, the tip surface data generator 126 generates a pair of a drill tracker transform and a segmentation for a given angle. A plurality of pairs of the drill tracker transforms and a segmentation corresponding to respective view angles is obtained from the stereo camera system as the drill tip 110 is rotated. Further, a space carving type algorithm may be used to reconstruct the drill tip surface data in three-dimensional form.

In aspects, the tip surface data generator 126 performs principal components analysis (hereinafter "PCA") of data points in a three-dimensional space to reconstruct the main cutting plane as a cutting surface. An orthogonal plane of symmetry may be computed using the symmetry constraint of the drill tip 110. The plane data may be used for displaying the drill tip 110 as three-dimensional graphical rendering. After the surface reconstruction, cutting edge contour, and cutting planes are computed, guidance can be done on the drill tip 110.

Traditional systems have been limited to only being able to determine a length of the drill 108. The present technology enables the processor to measure the diameter and more complex shapes of the drill tip 110.

The guidance data generator 128 generates guidance data to use the drill tip 110 of the drill 108 during a surgical procedure. In aspects, the guidance data includes the tip surface data of the tip, a cutting edge contour of the tip, and the plane data of the tip.

The drill tip database 130 stores data describing functions and characteristics of drill tips and drills being calibrated. In aspects, the drill tip database 130 indexes data by an identifier of a respective drill and a drill tip, a type of functions of drill tips, and other searchable attributes. In some aspects, the drill tip database 130 further stores three-dimensional surface data of drill tips upon completion of the calibration for retrieval during navigation of surgical operations using the drill tip.

As will be appreciated, the various methods, devices, applications, features, etc., described with respect to FIG. 1 are not intended to limit the system 100 to being performed by the particular applications and features described. Accordingly, additional controller configurations may be used to practice the methods and systems herein and/or features and applications described may be excluded without departing from the methods and systems disclosed herein.

Figure 2:
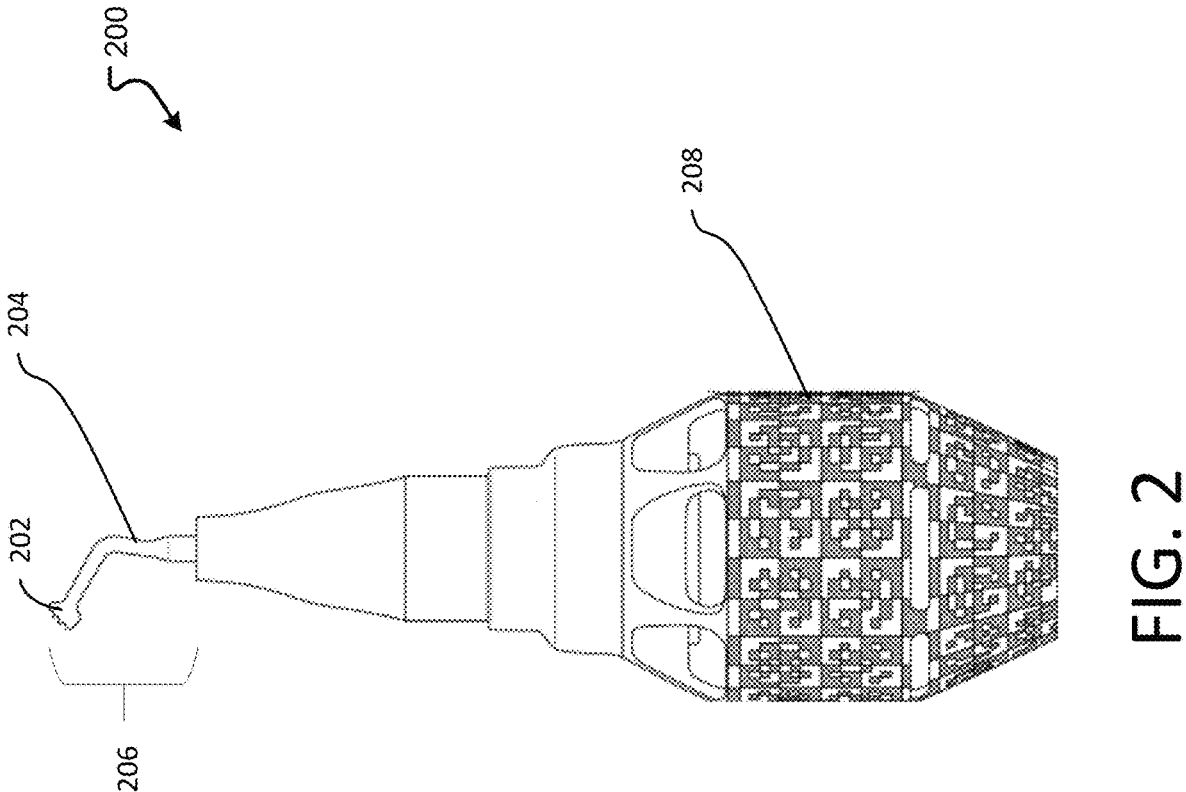
FIG. 2 illustrates an example of a drill according to an embodiment of the invention.

FIG. 2 illustrates an example of a drill according to an embodiment of the invention. In aspects, the drill 200 includes drill tip 202 (e.g., the drill tip 110 as shown in FIG. 1), stem 204, tool bit 206, and drill tracker 208. The calibration operation according to the present technology measures a cutting edge of the drill tip 202, a cutting edge contour of the drill tip 202, and reconstructs a three-dimensional shape of the drill tip 202.

The stem 204 represents a prolonged section of the tool bit 206 between the drill tip 202 and a root of the tool bit 206. The drill tracker 208 is a part of a handpiece of the drill 200. The drill tracker 208 includes a printed optically detectable pattern used for determining and tracking a position and an angle of the drill during a calibration and during a navigation of a surgical procedure. In aspects, the drill tip 202 includes a piezoelectric drill tip, which moves at a piezoelectric ultrasonic frequency.

As will be appreciated, the drill tip 202 described with respect to FIG. 2 are not intended to limit use of the example 200. Accordingly, additional and/or alternative examples may be used to practice the methods and systems herein and/or features and applications described may be excluded without departing from the methods and systems disclosed herein.

FIG. 3A illustrates an example graphical image for selecting the drill according to an embodiment of the invention. Drill 300A includes drill tip 302 (e.g., the drill tip 202 as shown in FIG. 2) and a stem 304 (e.g., the stem 204 as shown in FIG. 2). In aspects, the drill tip 302 moves at a piezoelectric ultrasound frequency to cut a target area during a surgical procedure.

FIG. 3B illustrates an example user interface depicting captured images used to define a location of a tip of the drill and rocking the drill at the tip according to an embodiment of the invention Example image 300B includes a drill tip 302 of a drill 310. The image further depicts a reference sheet (e.g., the reference sheet 106 as shown in FIG. 1) and a center mark 314 of the reference sheet 312.

The reference sheet 312 may be a surface of a flat plate or other object or may be a decal on placard that is adhered to the object. The pattern on the reference sheet 312 is an optically visible pattern that can be detected and captured by the stereo camera 102 and from which the computer processor can determine features about the pattern. In aspects, the reference sheet 106 may indicate a checkerboard pattern of contrasting (e.g., white and black) squares, rectangles or other polygonal shapes. Each section of the pattern may indicate distinct pattern of white polygonal shapes and distinct black polygonal shapes. In aspects, the pattern some of sections of the pattern may be identical so long as the reference sheet indicates shapes of alternating colors or shades that function to provide contrast to one another so that edges of the shapes can be detected.

Figures 3C, 3D:
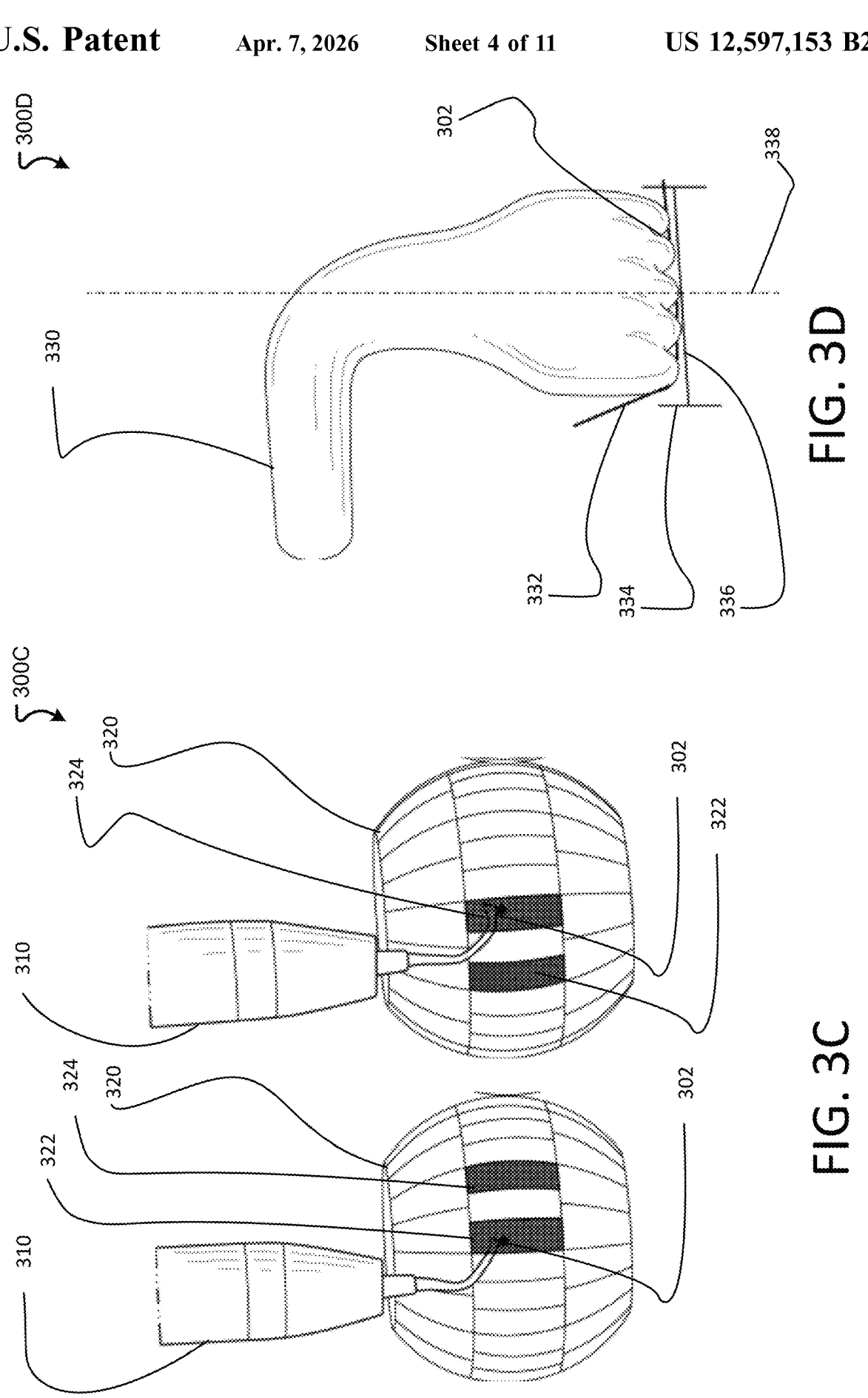
FIG. 3C illustrates an example graphical user interface depicting captured images used to measure a three-dimensional shape of the drill by rotating the drill according to an embodiment of the invention.
FIG. 3D illustrates a three-dimensional shape reconstruction of the drill according to an embodiment of the invention.

FIG. 3C illustrates an example graphical image depicting captured images used to measure a three-dimensional shape of the drill by rotating the drill according to an embodiment of the invention. Example image 300C indicates two images in sequence as a drill is rotated. In aspects, the example image 300C includes a drill 310 and a drill tip 302, a generated spherical shape 320. As the drill 310 is rotated at the drill tip 302, the generated spherical shape 320 turns. The spherical shape 320 includes segmented areas that are placed in three rows around the spherical shape 320. As the drill 310 is rotated, the spherical shape 320 turns and indicates distinct sections that correspond to the drill tip 302. For example, the highlighted area changes from one area 322 to another area 324 in the same middle row. Other areas in other rows are highlighted as the drill 310 is rotated in various angles and the data is captured. In aspects, the present technology completes capturing of frames of image data of the drill tip when all of the areas on the spherical shape 320 becomes highlighted. Hence, when all the areas of the spherical shape 320 are highlighted, it indicates to the use that the capturing is complete. Other methods of providing a visual indication to the user of the status or completeness of the image data capture can be used, such as bar graphs, or graphical indicators (e.g., arrows, etc.).

FIG. 3D illustrates a three-dimensional shape reconstruction of the drill according to an embodiment of the invention. The three-dimensional shape 300D of the drill tip includes a drill tip 302 and a stem 330. The three-dimensional shape 300D further indicates a cutting edge contour 332, a cutting edge plane 334, a cutting edge 336, and a vertical symmetric line 338.

Figure 3E:
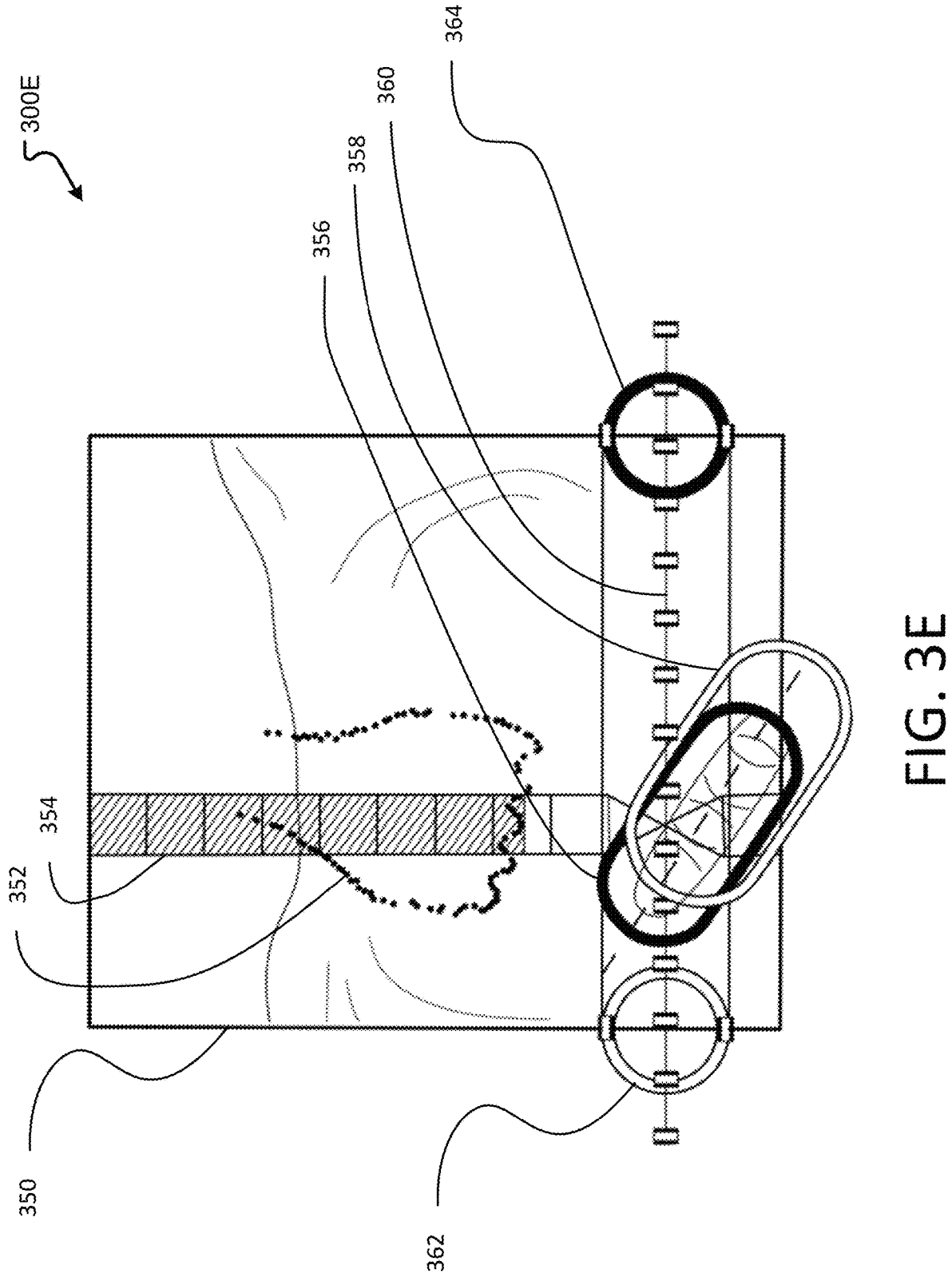
FIG. 3E illustrates an example graphical user interface to assist a surgical procedure depicting in the upper images the features corresponding to the shape, location and orientation of the drill bit using the drill according to an embodiment of the invention.

FIG. 3E illustrates an example graphical user interface to assist in a surgical procedure by navigating placement of the drill tip. In aspects, the example graphical user interface 300E indicates a close-up rendering of a cavity in an area inside a mouth of a dental patient. In aspects, the surgical procedure includes a cutting or drilling operation using the drill tip. The terms cutting and drilling are used interchangeably herein. An area inside a defined boundary such as a rectangular boundary 350 indicates an area of interest for navigating the surgical procedure. In aspects, the rectangular boundary 350 is based on the pre-planned drilling location relative to a location of the tooth. An edge shape 352 indicates a current location of a drill tip (e.g., the drill tip 302 as shown in FIG. 3A-D) in real time. In some aspects, a location of the rectangular boundary 350 remains fixed (for example. relative to the patient's jaw) as the drill tip moves. In some other aspects, a display of the boundary may be enlarged as the user zooms in the boundary as the display of the rendering of the cavity is enlarged. A gauge 354 indicates a distance (depth) between the current drill tip location and a defined end point of cutting/drilling during the drilling operation (e.g., the final planned depth). In aspects, the shadowed area of the gauge 354 increases (fills) as the depth of the drill tip gets closer to the preplanned end point of the drilling operation.

The current (or actual) angular position indicator 356, shown in FIG. 3E as a dark oval shape, indicates the current angular position of the drill tip. The target angular position indicator 358, depicted in a lighter or different color or shade oval shape, indicates a target angular position based on the predetermined plan and provides a visual indicator for the user to move the drill tip towards during the drilling operation for cutting in order to accomplish the pre-planned procedure. A planned cutting line 360 indicates a line along which the user should try to position the drill tip to cut. A first end point 362 indicates an end point of a pair of end points of the planned cutting line 360. A second end point 364 indicates the other end point of the pair of end points of the planned cutting line 360.

As will be appreciated, the drill tip 302 described with respect to FIGS. 3A-3D are not intended to limit use of the examples 300A-300E. Accordingly, additional and/or alternative examples may be used to practice the methods and systems herein and/or features and applications described may be excluded without departing from the methods and systems disclosed herein.

FIG. 4A illustrates an example reconstruction volume shape generated about a drill tip of a drill according to the present invention. Example 400A indicates a drill 402, a drill tip 404, a reconstruction volume shape 406. In aspects, the reconstruction volume shape 406, illustrated as a rectangular wireframe, is fixed to the center mark 410 of the reference sheet 408. The drill tip 404 touches and is held at the center mark 410 of the reference sheet 408 for at least a predetermined time. A processor processes a relative transform of coordinate data between the reconstruction volume shape 406 and the drill tracker of the drill 402 (the drill tracker not shown in FIG. 4A; the drill tracker 208 is as shown in FIG. 2). In aspects, the reconstruction volume shape 406 is in rectangular prism form and describes the bounds of the drill tip. Accordingly, the drill tip remains inside the bounds of the reconstruction volume shape 406. In some aspects, a shape of the reconstruction volume shape 406 is not limited to the rectangular prism form to contain the shape of the drill tip within the reconstruction volume shape 406. In some aspects, A space carving process using the space carving algorithm includes carving away portions of the reconstruction volume shape 406 that are not part of the drill tip until the final tip surface in three-dimensional form remains.

In aspects, as described previously, the reference sheet 408 is a flat surface with printed patterns as trackable fiducial markers. After computing the relative transform between the reconstruction volume shape 406 and the drill tracker printed on the drill 402, the reconstruction volume shape 406 "follows" the drill 402 by maintaining relative positions of the drill tracker. Accordingly, the drill tip 404 resides inside the reconstruction volume shape 406 as the drill tip 404 moves. As such, the reconstruction volume shape 406 represents a relative frame of reference in capturing edge points of the drill tip 404. The edge points of the drill tip 404 become the basis to determine a cutting edge contour of the drill tip 404 and a cutting edge plane of the drill tip 404. In aspects, the captured points in a three-dimensional coordinate system become the basis to reconstruct a three-dimensional shape data of the drill tip 404.

FIG. 4B illustrates example data points of planes tangent to the cutting edge of the drill tip of the drill according to the present invention. As the user moves the drill tip (e.g., the drill tip 404 as shown in FIG. 4A) along the cutting edge in a rocking motion on the reference sheet, the system computes planes that are tangent to the cutting edge. In aspects, each rock motion generates one contour along the edge of the drill tip (e.g., a contour 420A and another contour 420B as shown in FIG. 4B). In aspects, the present technology determines an edge contour of the drill tip by superimposing the contours.

FIG. 4C illustrates combined example data points of contours to determine edge contour data of the drill tip of the drill according to the present invention. Combining a plurality of contours (e.g., a contour 420A and another contour 420B, and the like in FIG. 4B) results in determining a cutting edge contour 422 of the drill tip as shown in FIG. 4C. The generated cutting edge contour 424 is super-imposed on a three-dimensional reconstruction of a shape of the drill with the drill tip 404 as shown in FIG. 4D.

As will be appreciated, the edge contour determination as described with respect to FIGS. 4A-4D are not intended to limit use of the examples 400A-400D. Accordingly, additional and/or alternative examples may be used to practice the methods and systems herein and/or features and applications described may be excluded without departing from the methods and systems disclosed herein.

Figures 5A, 5B:
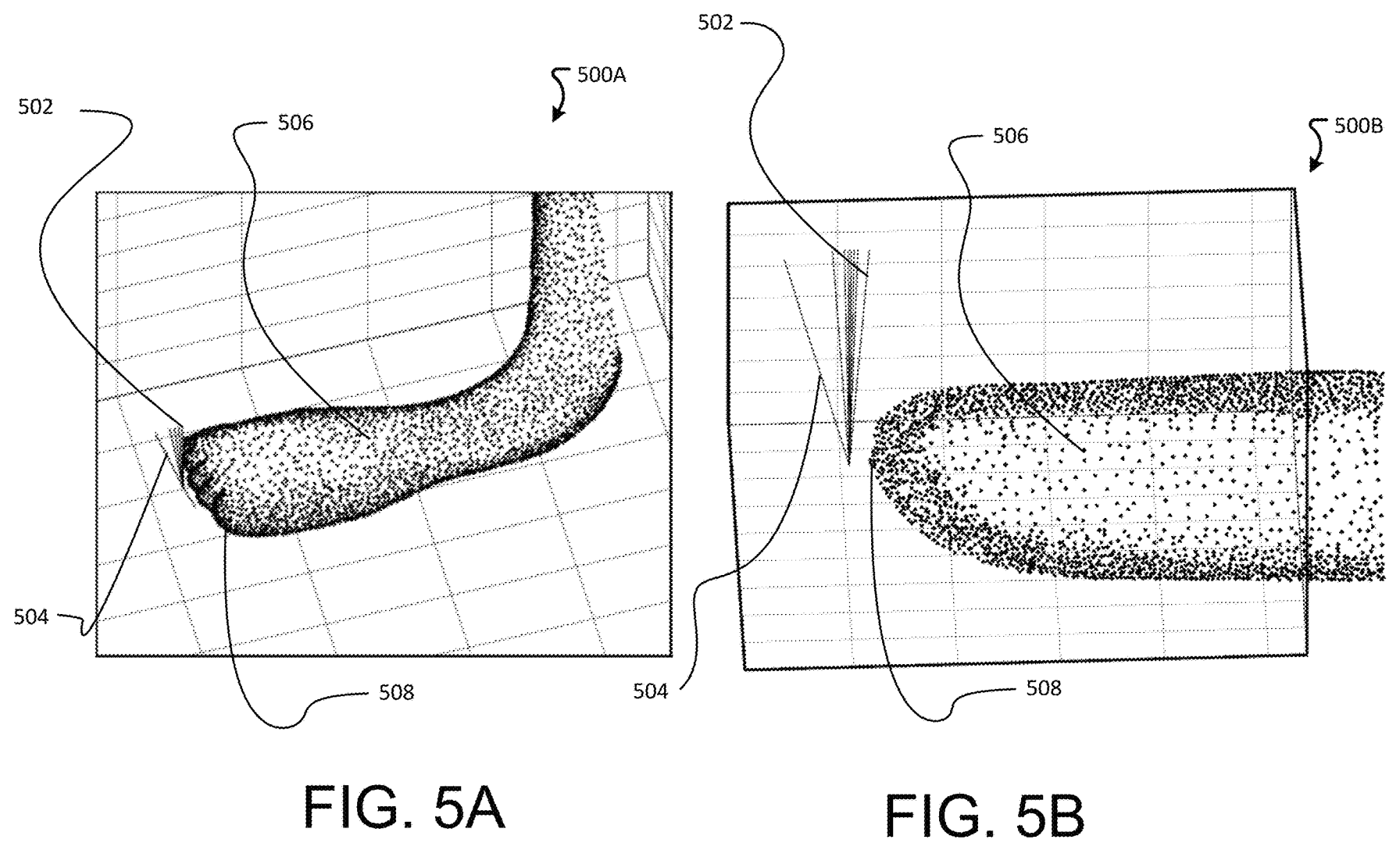
Figures 5C, 5D:
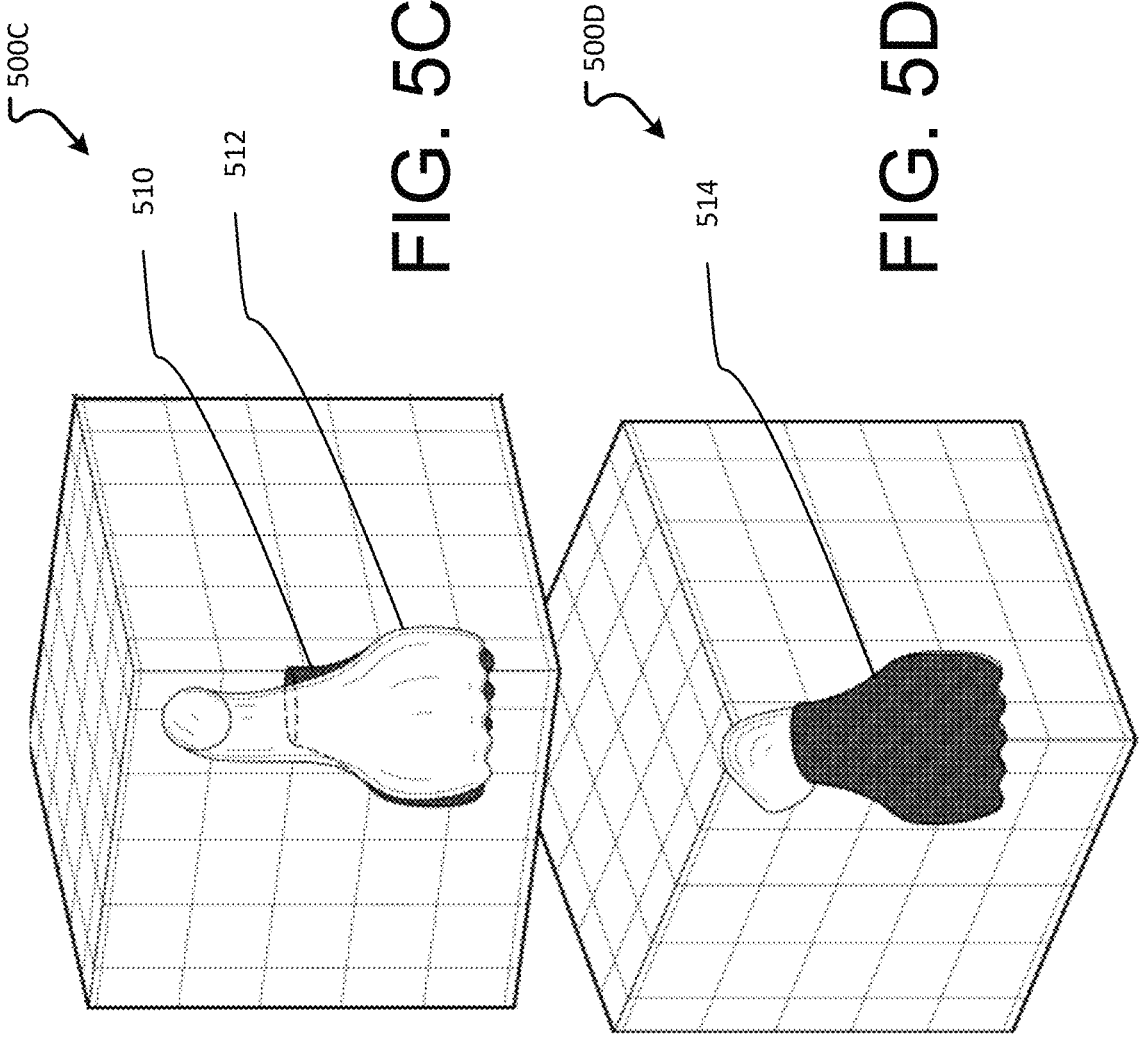
FIGS. 5C-D illustrate example orthogonal planes of symmetry of the reconstructed tip of the drill according to the present invention overlaid on an image of the actual tip.

FIGS. 5A-5F illustrate steps in processing captured points in a three-dimensional space to generate a three-dimensional reconstruction of a surface image of the drill tip. The steps further determine a cutting edge contour and the cutting plane. FIGS. 5A-B illustrate an example of the reconstructed main cutting plane and cutting surface of the tip of the according to the present invention.

FIG. 5A illustrates an example of a result 500A of the statistical analysis (e.g., using, but not limited to, Principal Component Analysis (PCA)) of points (e.g., a point 506 in a three-dimensional point cloud) to reconstruct a three-dimensional shape of the drill tip 508 and a main cutting plane. PCA is well known to those skilled in the art and is described in a web page (en.wikipedia.org/wiki/Principal_component_analysis), which is incorporated herein by reference in its entirety.

Line 502 and edge 504 are on a plane that is tangent to the drill tip 508. The main cutting plane is a plane along which the drill tip cuts into. An edge 504 represents an edge of main cutting plane. The edge 504 also represents a line of cut movement of the drill tip 508, for example at a piezoelectric ultrasound frequency. The line 502 is perpendicular to the edge 504. The main cutting plane (i.e., a plane orthogonal to the tip) represents a plane along which the drill tip 508 cuts through an object. In aspects, the tip axis is perpendicular to an axis of cut movement according to the line 502 and the edge 504. FIG. 5B illustrates an enlarged view 500B of the drill tip 508 in a side view.

Figures 5E, 5F:
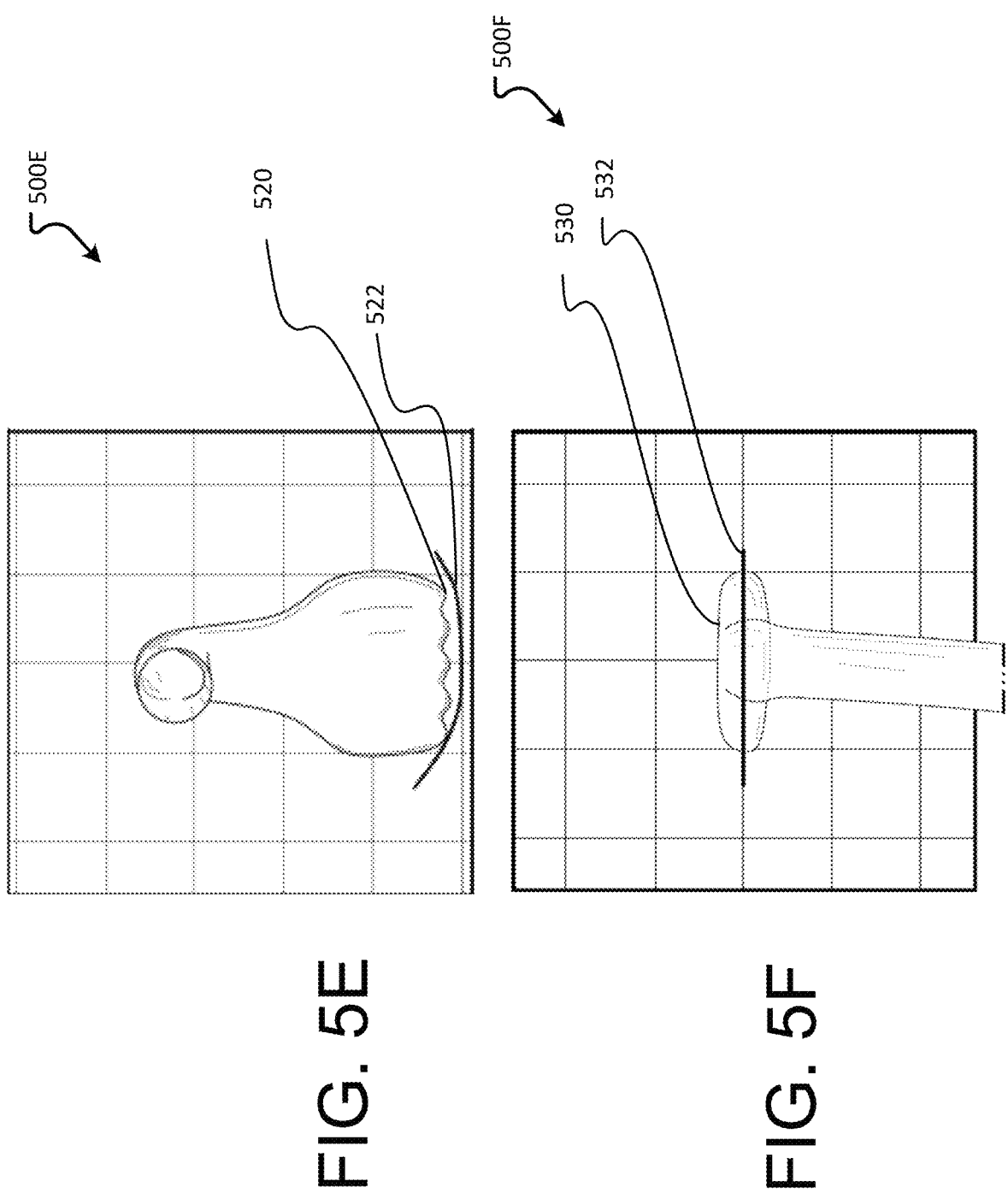
FIGS. 5E-F illustrate example three-dimensional surface data and the final planes according to the present invention.

FIGS. 5C-D illustrate examples of orthogonal planes of symmetry of the reconstructed drill tip according to the present invention. A first view 500C and a second view 500D show a result of computing the plane of left/right symmetry using two orthogonal planes of the drill tip by overlaying images of the actual drill tip. The two overlaid three-dimensional shapes (510 and 512) represent a same drill tip that is flipped over by 180 degrees about the cutting plane (e.g., the main cutting plane). The two shapes are registered together (i.e., a shape 514 as shown in FIG. 5D). Superimposing and matching the two shapes enables computing the two orthogonal planes of right/left symmetry of the drill tip. Further, the two orthogonal planes become the basis for computing the tip axis (e.g., the tip axis 532 as shown in FIG. 5F). In aspects, the cutting edge of the drill tip has an x-y symmetrical shape as a predetermined symmetry constraint of the drill tip.

FIGS. 5E-F illustrate example three-dimensional surface data and a cutting contour and cutting planes according to the present invention. In FIG. 5E, the example three-dimensional surface data 500E represents a three-dimensional view of a drill tip in an orientation facing against a tip axis (not shown). The example 500E indicates a drill tip 520 and cutting edge contour 522 of the drill tip 520. In aspects, the tip axis obtained from computing the orthogonal planes of the drill tip in FIG. 5D enables determining an orientation of the drill tip 520 in the three-dimensional space to display the cutting edge contour 522.

FIG. 5F indicates an example three-dimensional surface data 500F in an orientation orthogonal to tip axis 532. The example three-dimensional surface data 500F indicates drill tip 530 and the tip axis 532. Specifically, the tip axis 532 runs "through the page" of FIG. 5F. In aspects, the view as illustrated in FIG. 5F is displayed to the user during the surgical procedure in a three-dimensional graphic display.

As will be appreciated, the reconstruction of the three-dimensional shape of the drill tip described with respect to FIGS. 5A-4F are not intended to limit use of the examples 500A-F00D. Accordingly, additional and/or alternative examples may be used to practice the methods and systems herein and/or features and applications described may be excluded without departing from the methods and systems disclosed herein.

Figure 6:
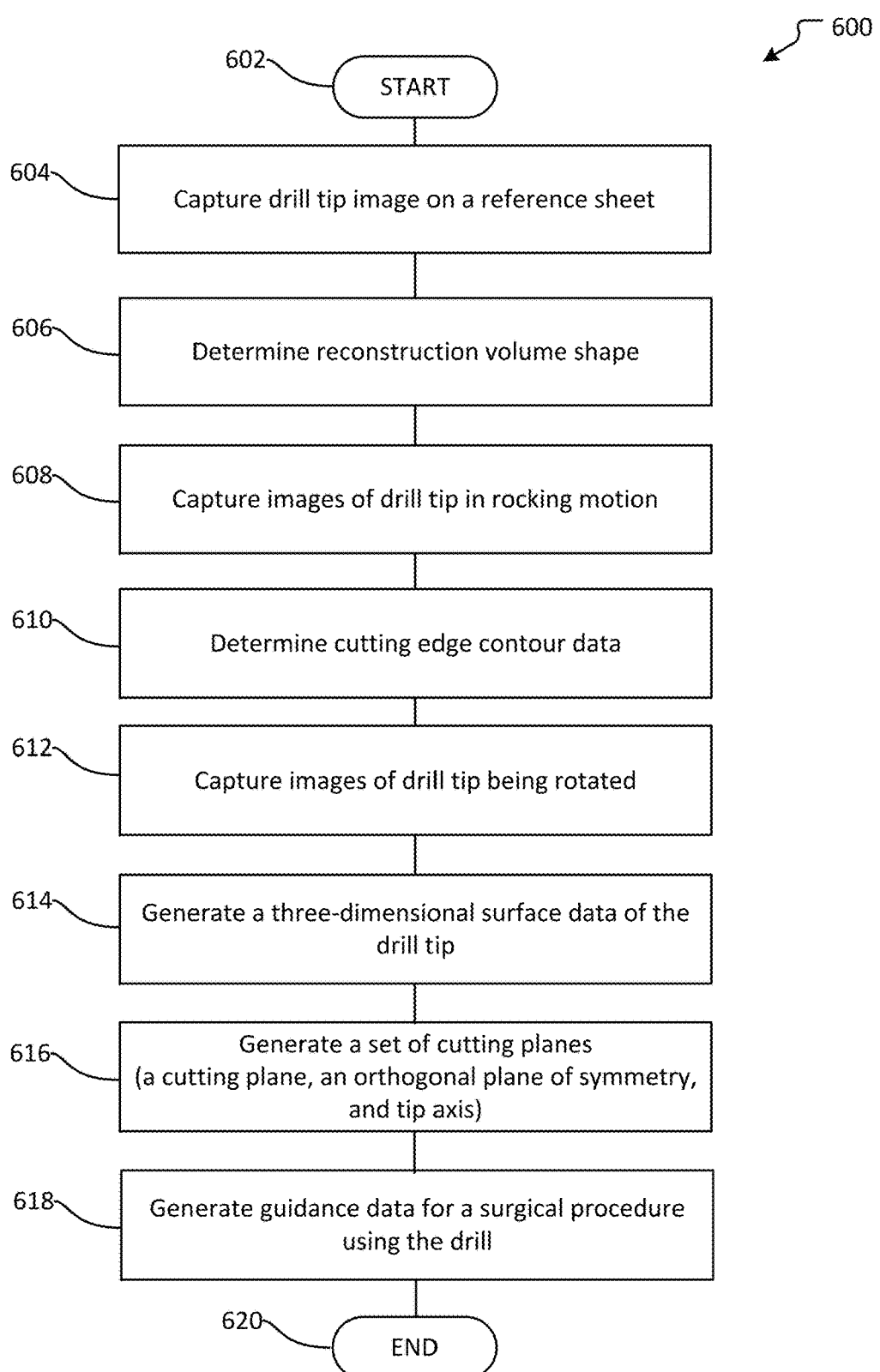
FIG. 6 illustrates an example method for generating guidance data according to the present invention

FIG. 6 illustrates an example method for generating guidance data according to the present invention. The present invention allows for measuring and calibrating a drill tip with curved and complex shapes. A general order of the operations for the example method 600 is shown in FIG. 6. Generally, the method 600 begins with start operation 602 and ends with end operation 620. The method 600 may include more or fewer steps or may arrange the order of the steps differently than those shown in FIG. 6.

The method 600 can be executed as a set of computer-executable instructions executed by a cloud system and encoded or stored on a computer readable medium. Further, the method 600 can be performed by gates or circuits associated with a processor, an ASIC, an FPGA, a SOC or other hardware device. Hereinafter, the method 600 shall be explained with reference to the systems, components, devices, modules, software, data structures, data characteristic representations, signaling diagrams, methods, etc., described in conjunction with FIGS. 1, 2, 3A-3E, 4A-4C, 5A-5F, and 7.

Following start operation 602, the method 600 begins with capture operation 604, which includes capturing image data that includes a drill tip on a reference sheet (e.g., capturing image data of the drill tip 302 placed at the center mark 314 on the reference sheet 312 as shown in FIG. 3B). In aspects, the reference sheet indicates a pattern that may be used as a reference point and a reference region to determine an orientation of the drill tip. In further aspects, the capture operation 604 is performed by using a camera. The camera may include a stereo camera.

At determine reconstruction volume shape operation 606, a shape of a reconstruction volume is determined. In aspects, the reconstruction volume shape (e.g., the reconstruction volume shape 406 as shown in FIG. 4A) may indicate a rectangular wireframe shape that includes the stem and the drill tip of the drill inside the reconstruction volume shape. The reconstruction volume shape enables the system to track a location of the drill tip for calibration.

At capture image of the drill tip in rocking motion operation 608, a plurality of frames of image data with the drill tip in a rocking operation may be captured. The frames of image data may indicate the drill tip in varying angles of views as the user tilts the drill tip back and forth in a rocking motion (i.e., rocking the drill tip).

At determine cutting edge contour data operation 610, cutting edge contour data is determined. The cutting edge contour corresponds to a contour line that represents a cutting edge of the drill tip. (e.g., the cutting edge contour 422 as shown in FIG. 4C.)

At capture image of the drill tip in rotation operation 612, a plurality of frames of image data of the drill tip are captured. In particular, the captured plurality of frames of image data indicates the drill tip in varying angles of views as the user rotates the drill tip along the axis of the drill tip (e.g., the example of rotating the drill tip 302 as shown in FIG. 3C) is captured.

At generate a three-dimensional surface data operation 614, a three-dimensional surface data of the drill tip is generated (e.g., the three-dimensional shape of the drill tip in example 300D as shown in FIG. 3D, example 500E as shown in FIG. 5E, and the example 5F as shown in FIG. 5F. In aspects, the generate a three-dimensional surface data operation 614 further comprises performing a principal component analysis (PCA) of the captured three-dimensional points.

At generate a set of cutting planes operations 616, a set of cutting planes is generated. In aspects, the cutting planes include a cutting plane of the drill tip, an orthogonal plane of symmetry of the drill tip, and a horizontal plane of the drill tip. The cutting plane of the drill tip represents two-dimensional planar data that indicates a plane along which the drill tip cuts through a target object.

At generate guidance data operation 618, guidance data for performing a surgical procedure by using the drill tip is generated. In aspects, the generate guidance data operation 618 further includes storing the generated guidance data in a drill tip database (e.g., the drill tip database 130 as shown in FIG. 1). In aspects, the generate guidance data includes data that describes the drill tip in a three-dimensional space for use in navigating a surgical procedure. (e.g., the example graphical user interface as shown in FIG. 3E.) The method 600 ends with the end operation 620.

As should be appreciated, operations 602-620 are described for purposes of illustrating the present methods and systems and are not intended to limit the disclosure to a particular sequence of steps, e.g., steps may be performed in different order, additional steps may be performed, and disclosed steps may be excluded without departing from the present disclosure.

Figure 7:
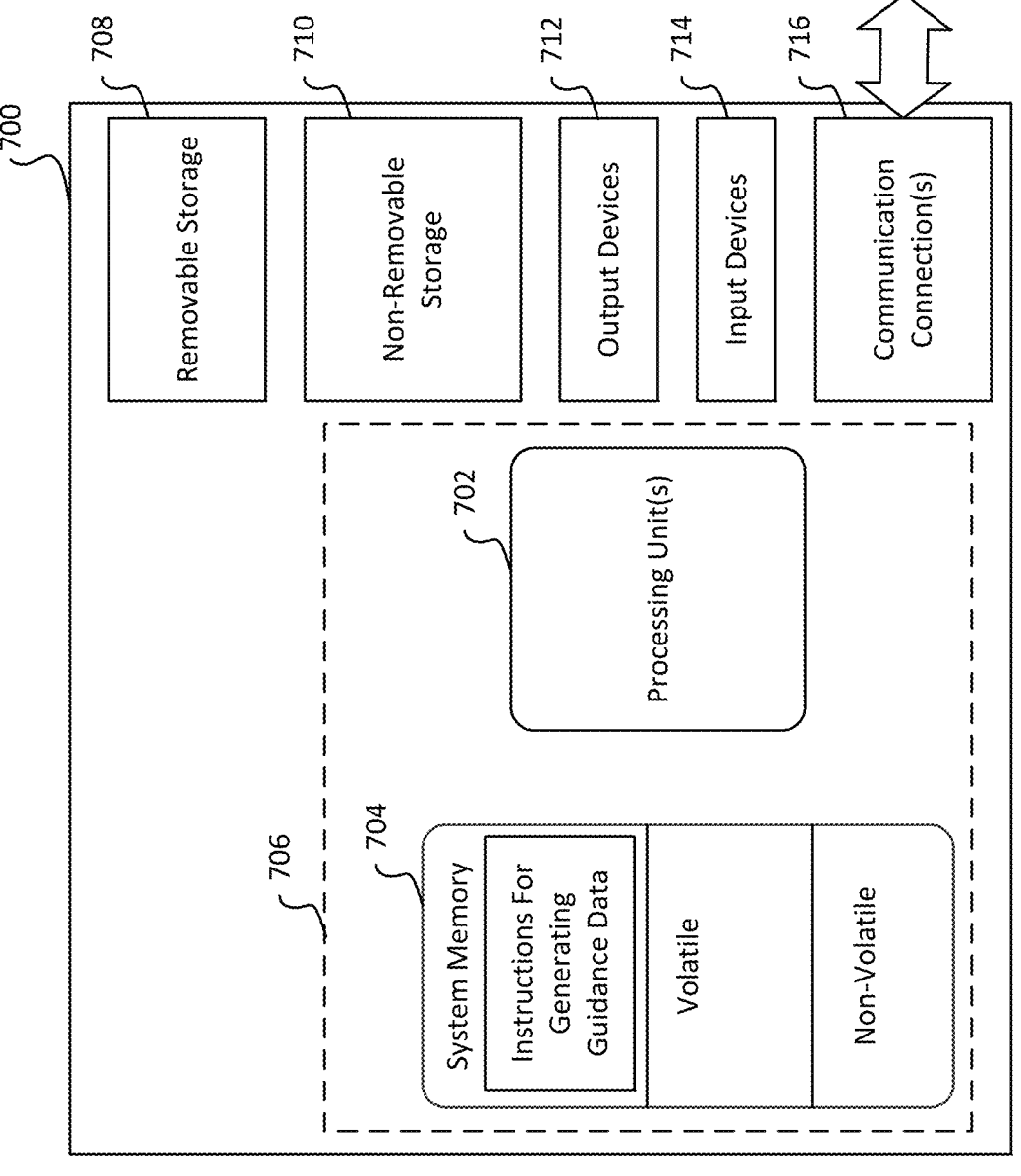
FIG. 7 illustrates a simplified block diagram of a device with which aspects of the present disclosure may be practiced in accordance with aspects of the present disclosure.

FIG. 7 illustrates a simplified block diagram of a device with which aspects of the present disclosure may be practiced in accordance with aspects of the present disclosure. The device, which represents at least a part of an example surgical navigation system, may be a workstation and/or a mobile computing device, for example. One or more of the present embodiments may be implemented in an operating environment 700. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smartphones, network PCs, minicomputers, mainframe computers, distributed computing environments that include any of the above systems or devices, and the like.

In its most basic configuration, the operating environment 700 typically includes at least one processing unit 702 and memory 704. Depending on the exact configuration and type of computing device, memory 704 may be volatile (such as RAM), non-volatile (such as ROM, flash memory, etc.), or some combination of the two. This most basic configuration is illustrated in FIG. 7 by dashed line 706. Further, the operating environment 700 may also include storage devices (removable, 708, and/or non-removable, 710) including, but not limited to, magnetic or optical disks or tape. Similarly, the operating environment 700 may also have input device(s) 714 such as remote controller, keyboard, mouse, pen, voice input, on-board sensors, etc. and/or output device(s) 712 such as a display, speakers, printer, motors, etc. Also included in the environment may be one or more communication connections 716, such as LAN, WAN, a near-field communications network, a cellular broadband network, point to point, etc.

Operating environment 700 typically includes at least some form of computer readable media. Computer readable media can be any available media that can be accessed by the at least one processing unit 702 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible, non-transitory medium which can be used to store the desired information. Computer storage media does not include communication media. Computer storage media does not include a carrier wave or other propagated or modulated data signal.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

The operating environment 700 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

As will be understood from the foregoing disclosure, one aspect of the technology relates to a method of calibrating a tip on an instrument. The method comprises steps of: capturing a first set of image data using at least one camera, wherein the first set of image data includes the instrument, and the instrument includes the tip and a stem connected to the tip; generating, based on the first set of image data, a reconstruction volume shape of the tip; capturing a second set of image data using the at least one camera; determining, based on a plane along an edge of the tip and the reconstruction volume shape, cutting edge contour data of the tip; capturing a third set of image data using the at least one camera; generating, based on the third set of image data, three-dimensional tip surface data of the tip; generating, based on the three-dimensional tip surface data of the tip, a set of cutting planes; generating, based on the set of cutting planes, guidance data for use in navigating a surgical procedure using the instrument; and storing the guidance data in a tip database. The first set of image data depicts the tip of the instrument touching a reference sheet and geometric pattern data indicated on the instrument, and the first set of image data includes a plurality of image frame data. The reconstruction volume shape represents a bounding box sized to include the tip and the stem of the instrument, and a location of the tip is on a surface of the reconstruction volume shape. The second set of image data corresponds to the tip repeatedly tilting along the plane along the edge of the tip, the tip is at a center of the tilting. The third set of image data indicates the tip rotating relative to a longitudinal axis of the stem of the instrument. The set of cutting planes includes a main cutting plane, an orthogonal plane of symmetry, and final planes, wherein the main cutting plane is based on the three-dimensional tip surface data of the tip using a Principal Component Analysis, the orthogonal plane of symmetry is based on symmetry constraint of the tip, and the final planes are based on a combination of the three-dimensional tip surface data of the tip of the instrument and the cutting edge contour data of the instrument. The guidance data includes data describing a location and orientation of the tip of the instrument for displaying on a display, and the guidance data includes the three-dimensional tip surface data and the set of cutting planes for displaying the three-dimensional tip surface data superimposed on the displayed image from the at least one camera in real time. The at least one camera includes a stereo camera. The tip represents a piezoelectric drill tip of a drill. The generating three-dimensional tip surface data comprises performing Principal Component Analysis on a plurality of three-dimensional points extracted from the third set of image data.

In another aspect, the technology relates to a system for calibrating a tip of an instrument. The system comprises a processor configured to execute operations comprising: capturing a first set of image data using at least one camera; generating, based on the first set of image data, a reconstruction volume shape of the tip; capturing a second set of image data using the at least one camera; determining, based on a plane along an edge of the tip and the reconstruction volume shape, cutting edge contour data of the tip; capturing a third set of image data using the at least one camera; generating, based on the third set of image data, three-dimensional tip surface data of the tip; generating, based on the three-dimensional tip surface data of the tip, a set of cutting planes; generating, based on the set of cutting planes, guidance data for use in navigating a surgical procedure using the instrument; and storing the guidance data in a tip database. The first set of image data depicts the tip of the instrument touching a reference sheet and geometric pattern data indicated on the instrument, and the first set of image data includes a plurality of image frame data.

In an embodiment, the reconstruction volume shape represents a bounding box sized to include the tip and the stem of the instrument, and a location of the tip is on a surface of the reconstruction volume shape. The second set of image data may correspond to the tip repeatedly tilting along the plane along the edge of the tip, the tip is at a center of the tilting, and the third set of image data indicates the tip rotating relative to a longitudinal axis of the stem of the instrument. The set of cutting planes includes a main cutting plane, an orthogonal plane of symmetry, and final planes, wherein the main cutting plane is based on the three-dimensional tip surface data of the tip using a Principal Component Analysis, the orthogonal plane of symmetry is based on symmetry constraint of the tip, and the final planes are based on a combination of the three-dimensional tip surface data of the tip of the instrument and the cutting edge contour data of the instrument. The guidance data includes data describing a location and orientation of the tip of the instrument for displaying on a display, and the guidance data includes the three-dimensional tip surface data and the set of cutting planes for displaying the three-dimensional tip surface data superimposed on the displayed image from the at least one camera in real time.

In further aspect, the technology relates to a device for calibrating a tip of an instrument. The device comprises a processor configured to execute operations comprising:

capturing a first set of image data using at least one camera; generating, based on the first set of image data, a reconstruction volume shape of the tip; capturing a second set of image data using the at least one camera; determining, based on a plane along an edge of the tip and the reconstruction volume shape, cutting edge contour data of the tip; capturing a third set of image data using the at least one camera; generating, based on the third set of image data, three-dimensional tip surface data of the tip; generating, based on the three-dimensional tip surface data of the tip, a set of cutting planes; generating, based on the set of cutting planes, guidance data for use in navigating a surgical procedure using the instrument; and storing the guidance data in a tip database. The first set of image data may depict the tip of the instrument touching a reference sheet and geometric pattern data indicated on the instrument, and the first set of image data includes a plurality of image frame data. The reconstruction volume shape preferably represents a bounding box sized to include the tip and the stem of the instrument, and a location of the tip is on a surface of the reconstruction volume shape. The second set of image data may correspond to the tip repeatedly tilting along the plane along the edge of the tip, the tip is at a center of the tilting, and the third set of image data indicates the tip rotating relative to a longitudinal axis of the stem of the instrument. The set of cutting planes preferably includes a main cutting plane, an orthogonal plane of symmetry, and final planes, wherein the main cutting plane is based on the three-dimensional tip surface data of the tip using a Principal Component Analysis, the orthogonal plane of symmetry is based on symmetry constraint of the tip, and the final planes are based on a combination of the three-dimensional tip surface data of the tip of the instrument and the cutting edge contour data of the instrument. The guidance data preferably includes data describing a location and orientation of the tip of the instrument for displaying on a display, and the guidance data includes the three-dimensional tip surface data and the set of cutting planes for displaying the three-dimensional tip surface data superimposed on the displayed image from the at least one camera in real time. The at least one camera includes a stereo camera. The tip preferably represents a piezoelectric drill tip of a drill. In an embodiment, the generating three-dimensional tip surface data further comprises performing Principal Component Analysis on a plurality of three-dimensional points extracted from the third set of image data.

Any of the one or more above aspects in combination with any other of the one or more aspect. Any of the one or more aspects as described herein.

The description and illustration of one or more aspects provided in this application are not intended to limit or restrict the scope of the disclosure as claimed in any way. The aspects, examples, and details provided in this application are considered sufficient to convey possession and enable others to make and use claimed aspects of the disclosure. The claimed disclosure should not be construed as being limited to any aspect, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate aspects falling within the spirit of the broader aspects of the general inventive concept embodied in this application that do not depart from the broader scope of the claimed disclosure.

The invention claimed is:

1. A method of calibrating a tip on an instrument using a microprocessor system, the method comprising steps of:
   capturing a first set of image data using at least one camera in communication with the microprocessor system, wherein the first set of image data includes the instrument, and the instrument includes the tip and a stem connected to the tip;
   generating, based on the first set of image data, a reconstruction volume shape of the tip;
   capturing a second set of image data of the tip of the instrument while the tip is moved using the at least one camera;
   determining, based on a plane along an edge of the tip captured in the second set of image data and the reconstruction volume shape, cutting edge contour data of the tip;
   capturing a third set of image data of the tip of the instrument while the tip is moved using the at least one camera;
   generating, based on the third set of image data, three-dimensional tip surface data of the tip;
   generating, based on the three-dimensional tip surface data of the tip, a set of cutting planes;
   generating, based on the set of cutting planes, guidance data for use in navigating a surgical procedure using the instrument; and
   storing the guidance data in a tip database on a non-transitory computer-readable medium.

2. The method according to claim 1, wherein the first set of image data depicts the tip of the instrument touching a reference sheet and geometric pattern data indicated on the instrument, and the first set of image data includes a plurality of image frame data.

3. The method according to claim 1, wherein the reconstruction volume shape represents a bounding box sized to include the tip and the stem of the instrument, and a location of the tip is on a surface of the reconstruction volume shape.

4. The method according to claim 1, wherein the second set of image data corresponds to the tip repeatedly tilting along the plane along the edge of the tip, the tip is at a center of the tilting.

5. The method according to claim 1, wherein the third set of image data indicates the tip rotating relative to a longitudinal axis of the stem of the instrument.

6. The method according to claim 1, wherein the set of cutting planes includes a main cutting plane, an orthogonal plane of symmetry, and final planes,
   the main cutting plane is based on the three-dimensional tip surface data of the tip using a Principal Component Analysis, the orthogonal plane of symmetry is based on symmetry constraint of the tip, and
   the final planes are based on a combination of the three-dimensional tip surface data of the tip of the instrument and the cutting edge contour data of the instrument.

7. The method according to claim 1, wherein the guidance data includes data describing a location and orientation of the tip of the instrument for displaying on a display, and
   the guidance data includes the three-dimensional tip surface data and the set of cutting planes for displaying the three-dimensional tip surface data superimposed on the displayed image from the at least one camera in real time.

8. The method according to claim 1, wherein the at least one camera includes a stereo camera.

9. The method according to claim 1, wherein the tip represents a piezoelectric drill tip of a drill.

10. The method according to claim 1, wherein the generating three-dimensional tip surface data further comprises performing Principal Component Analysis on a plurality of three-dimensional points extracted from the third set of image data.

11. A system for calibrating a tip of an instrument, the system comprises a non-transitory computer-readable recording medium and a microprocessor, the computer-readable recording medium including instructions that cause the processor to execute operations comprising:
   capturing a first set of image data using at least one camera, wherein the first set of image data includes the instrument, and the instrument includes the tip and a stem connected to the tip;
   generating, based on the first set of image data, a reconstruction volume shape of the tip;
   capturing a second set of image data of the tip of the instrument while the tip is moved using the at least one camera;
   determining, based on a plane along an edge of the tip captured in the second set of image data and the reconstruction volume shape, cutting edge contour data of the tip;
   capturing a third set of image data of the tip of the instrument while the tip is moved using the at least one camera;
   generating, based on the third set of image data, three-dimensional tip surface data of the tip;
   generating, based on the three-dimensional tip surface data of the tip, a set of cutting planes;
   generating, based on the set of cutting planes, guidance data for use in navigating a surgical procedure using the instrument; and
   storing the guidance data in a tip database.

12. The system according to claim 11, wherein the first set of image data depicts the tip of the instrument touching a reference sheet and geometric pattern data indicated on the instrument, and the first set of image data includes a plurality of image frame data.

13. The system according to claim 11, wherein the reconstruction volume shape represents a bounding box sized to include the tip and the stem of the instrument, and a location of the tip is on a surface of the reconstruction volume shape.

14. The system according to claim 11, wherein the second set of image data corresponds to the tip repeatedly tilting along the plane along the edge of the tip, the tip is at a center of the tilting, and the third set of image data indicates the tip rotating relative to a longitudinal axis of the stem of the instrument.

15. The system according to claim 11, wherein the set of cutting planes includes a main cutting plane, an orthogonal plane of symmetry, and final planes, the main cutting plane is based on the three-dimensional tip surface data of the tip using a Principal Component Analysis, the orthogonal plane of symmetry is based on symmetry constraint of the tip, and the final planes are based on a combination of the three-dimensional tip surface data of the tip of the instrument and the cutting edge contour data of the instrument.

16. The system according to claim 11, wherein the guidance data includes data describing a location and orientation of the tip of the instrument for displaying on a display, and the guidance data includes the three-dimensional tip surface data and the set of cutting planes for displaying the three-dimensional tip surface data superimposed on the displayed image from the at least one camera in real time.

17. A device for calibrating a tip of an instrument, the device comprises a non-transitory computer-readable recording medium and a microprocessor, the computer-readable recording medium including instructions that cause the processor to execute operations comprising:

capturing a first set of image data using at least one camera, wherein the first set of image data includes the instrument, and the instrument includes the tip and a stem connected to the tip;

generating, based on the first set of image data, a reconstruction volume shape of the tip;

capturing a second set of image data of the tip of the instrument while the tip is moved using the at least one camera;

determining, based on a plane along an edge of the tip captured in the second set of image data and the reconstruction volume shape, cutting edge contour data of the tip; capturing a third set of image data of the tip of the instrument while the tip is moved using the at least one camera;

generating, based on the third set of image data, three-dimensional tip surface data of the tip;

generating, based on the three-dimensional tip surface data of the tip, a set of cutting planes;

generating, based on the set of cutting planes, guidance data for use in navigating a surgical procedure using the instrument; and storing the guidance data in a tip database.

18. The device according to claim 17, wherein the first set of image data depicts the tip of the instrument touching a reference sheet and geometric pattern data indicated on the instrument, and the first set of image data includes a plurality of image frame data, the reconstruction volume shape represents a bounding box sized to include the tip and the stem of the instrument, and a location of the tip is on a surface of the reconstruction volume shape, the second set of image data corresponds to the tip repeatedly tilting along the plane along the edge of the tip, the tip is at a center of the tilting, and the third set of image data indicates the tip rotating relative to a longitudinal axis of the stem of the instrument.

19. The device according to claim 17, wherein the set of cutting planes includes a main cutting plane, an orthogonal plane of symmetry, and final planes, the main cutting plane is based on the three-dimensional tip surface data of the tip using a Principal Component Analysis, the orthogonal plane of symmetry is based on symmetry constraint of the tip, and the final planes are based on a combination of the three-dimensional tip surface data of the tip of the instrument and the cutting edge contour data of the instrument.

20. The device according to claim 17, wherein the guidance data includes data describing a location and orientation of the tip of the instrument for displaying on a display, and the guidance data includes the three-dimensional tip surface data and the set of cutting planes for displaying the three-dimensional tip surface data superimposed on the displayed image from the at least one camera in real time, the at least one camera includes a stereo camera, the tip represents a piezoelectric drill tip of a drill, and the generating three-dimensional tip surface data further comprises performing Principal Component Analysis on a plurality of three-dimensional points extracted from the third set of image data.

* * * * *